United States Patent [19]

Mane et al.

[11] Patent Number: 5,726,328
[45] Date of Patent: Mar. 10, 1998

[54] PREPARATION OF CIS-ISOAMBRETTOLIDES AND THEIR USE AS A FRAGRANCE

[75] Inventors: Maurice Mane, Magagnosc; Jean-Louis Ponge, Rouquier, both of France

[73] Assignee: V. Mane Fils S.A., France

[21] Appl. No.: 679,389

[22] Filed: Jul. 9, 1996

[51] Int. Cl.$^6$ .................................................. C07D 315/00
[52] U.S. Cl. ........................................ 549/266; 560/260
[58] Field of Search ........................... 560/266; 549/266

[56] References Cited

U.S. PATENT DOCUMENTS 3,681,395 8/1972 Mookherjee et al. .
4,014,902 3/1977 Tseng .

FOREIGN PATENT DOCUMENTS 1221105 4/1987 Canada .
0291067 5/1988 European Pat. Off. .

OTHER PUBLICATIONS

Magidson, Arch. Pharm. (Weinheim), Ges. 273,323 (1935).

J. Org. Chem. vol. 37, No. 24, pp. 3846–3848 (1972).

*Primary Examiner*—James H. Reamer
*Attorney, Agent, or Firm*—Larson & Taylor

[57] ABSTRACT

A method for the production of ω-haloalkyl esters which are useful as intermediates in the synthesis of cis-oxacycloheptadec-11-en-2-one (Product I) and cis-oxacycloheptadec-12-en-2-one (Product II). Also disclosed is a process for the synthesis of Products I–II and a method for using Products I–II to impart an ambery or musky smell to a fragrance composition. Finally, fragrance compositions including Products I–II are disclosed as well as end products such as perfume extracts, toilet waters, cosmetic preparations, soaps, detergents and functional products, each of which also contains at least one of Products I–II.

15 Claims, No Drawings

PREPARATION OF CIS-ISOAMBRETTOLIDES AND THEIR USE AS A FRAGRANCE

BACKGROUND OF THE INVENTION

1. Field of the Invention

The present invention relates to a process for the preparation of an ω-haloalkyl ester intermediate and the preparation of cis-isoambrettolides from the ω-haloalkyl ester intermediate. The present invention also relates to the use of cis-isoambrettolides in fragrance compositions and to a method of imparting a fragrance to a composition using cis-isoambrettolides.

2. Discussion of the Prior Art

The present invention relates, in a first aspect, to a process for the preparation of an ω-haloaliphatic ester by reacting an α-ω-alkanediol with an halohydric acid in the presence of an aliphatic carboxylic acid and an inert organic solvent which is capable of forming an azeotrope with water.

Magidson, Arch. Pharm. (Weinheim), Ges. 273, 323 (1935) relates to a process for the production of bromo-6-hexanol carboxylic ester wherein the alkyl group is preferably a methyl group. This product can be used in the process of the present invention for the production of 6-bromohexyl acetate, for example.

The present invention, in a second aspect, concerns the preparation of the cis-isoambrettolides cis-oxacycloheptadec-11-en-2-one (hereinafter "Product I") and cis-oxacycloheptadec-12-en-2-one (hereinafter "Product II") using a solid-liquid phase transfer reaction.

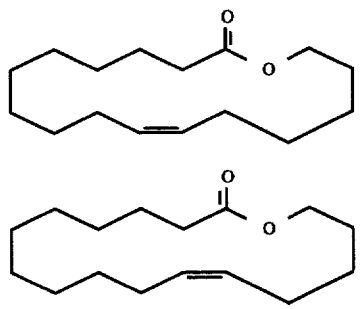

Oxacycloheptadec-12-en-2-one is mentioned as a by-product in a proposed synthesis of oxacycloheptadec-10-en-2-one in Mookherjee et al., *J. Org. Chem.*, Vol. 37, No. 24, pp. 3846–8 (1972) and U.S. Pat. No. 3,681,395. However, the synthetic pathway disclosed in this publication is designed to produce the trans-isomers and the author concludes that the predominant products are trans-isomers. This is confirmed by the fact that the olfactory properties of the products produced by this synthesis route are different than the olfactory properties of the cis-isomers.

Further, it is not feasible to produce either of Products I or II using the foregoing method since distillation cannot separate the conformational isomers and thereby rendering the production of products containing predominantly the cis-isomers nearly impossible. With this in mind, it is necessary to employ a synthesis method which produces products containing predominantly cis-double bonds since otherwise it will not be possible to produce products containing high concentrations of cis-isomers.

Canadian Patent no. 1,221,105 discloses the use of macrocyclic lactones to prepare ω-halogenated radioactive fatty acids for the recordation of medical images of the circulatory system. Among the compounds disclosed in this patent is cis-16-heptadec-11-enolide which is Product II as shown above. However, this patent does not disclose a synthesis route for making this product and thus the mere naming of this product, without more, is non-enabling for the person of skill in the art.

European Patent Application publication no. EP-A 291 067 discloses the use of macrocyclic lactones as complexing agents in the preparation of cyclo-octa-amylose using an enzymatic reaction.

Oxacycloheptadec-8-en-2-one cis (hereinafter "Product III") is the characteristic constituent of ambrette seed essential oil from the plant *Hibiscus abelmoschus*. This product is known for use in fragrance compositions but suffers the disadvantage that it is expensive because it is typically extracted from the natural product.

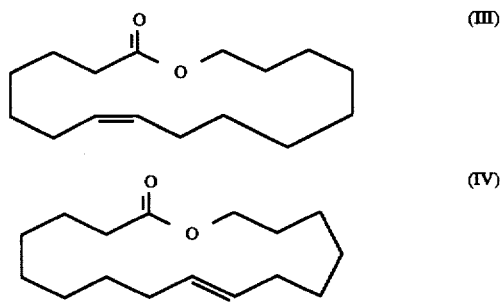

Another product which is currently available on the market is oxacycloheptadec-10-en-2-one trans (hereinafter "Product IV") in purified form. This product can be prepared by the method given in U.S. Pat. No. 4,014,902 (Tseng). However, this product does not possess the characteristic fragrant note of the natural cis-ambrettolide (Product III).

Some synthetic methods are known for the production of certain ambrettolides and/or isoambrettolides. For example, Mookherjee et al., *J. Org. Chem.*, Vol. 37, no. 24 pp. 3846–8 (1972) relates to a process for the synthesis of an isoambrettolide, namely, oxacycloheptadec-10-en-2-one. However, this process produces significant quantities of undesirable by-products and involves complex or expensive reagents.

Accordingly, there is a need in the art for fragrant musk compositions which employ less expensive ingredients and can be prepared in a simple and efficient manner from readily available raw materials.

SUMMARY OF THE INVENTION

The present invention relates, in a first aspect, to a process for the preparation of an ω-haloaliphatic ester by reacting an α-ω-alkanediol with an halohydric acid in the presence of an aliphatic carboxylic acid and an inert organic solvent which is capable of forming an azeotrope with water.

In a second aspect, the present invention relates to a process for the preparation of at least one product of the formulae I–II:

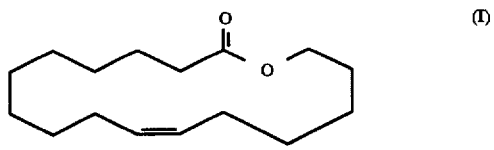

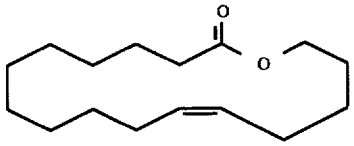

by condensing a phosphonium salt of an ω-haloaliphatic ester with a compound selected from aldehyde-alcohols or aldehyde-esters using a solid-liquid phase transfer reaction. This process may optionally further include one or both of the steps of preparing a phosphonium salt of an ω-haloaliphatic ester by reacting an ω-haloaliphatic ester with triphenylphosphine in an inert organic solvent and preparing the ω-haloaliphatic ester by reacting an α-ω-alkanediol with an halohydric acid in the presence of an aliphatic carboxylic acid in an inert solvent which is capable of forming an azeotrope with water.

In a third aspect, the present invention relates to a fragrance composition which is improved by incorporating therein at least one fragrant compound of the formulae I–II above, as well as to perfumes, toilet waters, cosmetic preparations, soaps, detergents, household products and industrial products including, but not limited to, air care products, toilet care products, surface care products, paints, masking agents for diesel fuels or gasoline, and heavy duty detergents which include either a compound of the formulae I–II or a fragrance composition as described above.

In another aspect, the present invention relates to a method of imparting an ambery or musky fragrance to a composition by incorporating in the composition an effective amount of at least one compound of the formulae I–II above to impart an ambery or musky fragrance to the composition.

The present invention provides a simple and efficient process for the production of synthetic compounds of the formulae I–II above which can be used to impart an ambery or musky fragrance to articles of manufacture.

Further objects and advantages of the invention will be apparent from the detailed description and examples which follow.

DETAILED DESCRIPTION OF THE PREFERRED EMBODIMENTS

Preparation of ω-Haloalkyl Esters

In a first embodiment, the present invention relates to a process for the preparation of ω-haloalkyl esters which are an intermediate product for the synthesis of the compounds of the formulae I–II:

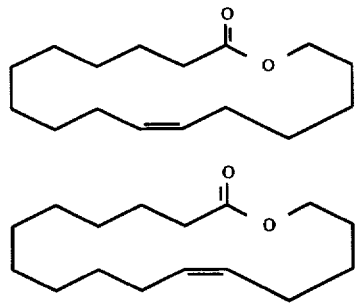

According to the present invention, the ω-haloalkyl carboxylic esters are prepared by treatment of an alkanediol with halohydric acid and an aliphatic carboxylic acid in the presence of an inert organic solvent which is capable of forming an azeotrope with water. Preferred organic solvents for this process include toluene, cyclohexane, methylcyclohexane, xylene and mixtures thereof.

The ω-haloalkyl carboxylic esters are preferably ω-halogenated carboxylic esters of $C_1$–$C_{20}$ alkyl groups. For the production of compounds of the formulae I–II, the alkyl group is preferaby either a hexyl group or an undecyl group. The preferred halogen for use in the ω-haloalkyl esters is bromine although other halogens may be employed, if desired.

The carboxylic ester group is preferably a $C_1$–$C_{10}$ alkyl ester group and most preferably the ester group is acetate. As a result, the preferred process of the present invention involves the reaction of an α-ω-$C_1$–$C_{20}$ alkanediol with bromohydric acid and a $C_1$–$C_{10}$ carboxylic acid. Most preferably, in the production of Product I, 1,6-hexanediol is reacted with bromohydric acid and acetic acid to produce 6-bromohexyl acetate which is useful as an intermediate in the synthesis of Product I.

In the most preferred process, a 48% bromohydric acid solution is employed. Water is removed from the reaction mixture by azeotropic distillation to obtain 6-bromohexyl acetate with approximately 86% purity and containing 3–4% of bromo-6-hexanol. The bromo-6-hexanol is acetylated with an approximately stoichiometric amount of acetic anhydride upon reflux to provide a crude material which contains more than 88% by weight of 6-bromohexyl acetate with the remainder including hexanediol-1,6-diacetate and dibromo-1,6-hexane. The dibromo-1,6-hexane and the hexanediol-1,6-diacetate can then be separated by vacuum distillation to obtain a 98% pure mixture of 6-bromohexyl acetate.

The dibromo-1,6-hexane by-product may optionally be transformed into 6-bromohexyl acetate by treatment with sodium acetate or potassium hydroxide in acetic acid as is described in the literature. The hexanediol-6-diacetate which was separated in the previous step may be recycled to the step of bromoacetylating the 1,6-hexanediol to yield additional 6-bromohexyl acetate.

Preparation of Product I (cis-oxacycloheptadec-11-en-2-one)

The 6-bromohexyl acetate is first converted to a phosphonium salt by, for example, reaction with triphenylphosphine in an organic solvent media. Conversion to the phosphonium salt generally requires about 16 hours of reflux with stirring whereby a solution of the triphenyl phosphonium salt of 6-bromohexyl acetate is obtained. Other conventional methods of preparing phosphonium salts may also be employed.

The next step in the preparation of Product I is the preparation of a sixteen carbon atom chain with a cis-ethylenic bond. This step is carried out by using a Wittig-type reaction and can be performed by direct addition of an aldehyde-ester reagent to a solution of the phosphonium salt which may be obtained directly from the previous step in the reaction or can be prepared as needed. More particularly, a solid-liquid phase transfer reaction is employed.

The 6-bromohexyl acetate is preferably reacted with oxo-10-decanoate in the phase transfer reaction to produce Product I. Oxo-10-decanoate can be prepared by ozonolysis of the corresponding undecylenate followed by a reduction reaction in accordance with known, conventional methods such as are described in *J. Org. Chem.*, Vol. 47, pp. 163–167 (1982); *J. Chem. Soc. Perkin Trans*, Vol. 1, pp. 161–168 (1986); and Tetrahedron Letters, Vol. 23, No. 51, pp. 5455–5458 (1982). It is preferable to use the methyl ester of undecylenic acid since this is a commercially available product.

The phase transfer reaction is carried out in the presence of a salt selected from alkali metal carbonates and alkaline earth metal carbonates. The most preferred salt for use in the phase transfer reaction is potassium carbonate. The preferred solvents for the phase transfer reaction are toluene, cyclohexane, methyl-cyclohexane, dioxane, dichloro-1,2-ethane and mixtures thereof. The solvent media may also optionally include a lower aliphatic alcohol.

The phase transfer reaction is carried out at a temperature of 60°–130° C. in a slightly aqueous organic medium. The reaction temperature will be a function of the solvent media employed for the reaction. For example, when the reaction is carried out in the preferred solvent, toluene, the reaction temperature will be between 110°–125° C. The aldehyde-ester can be added to the phosphonium salt solution all at once or dropwise over an extended period.

Optionally, a phase transfer catalyst may be added to the reaction mixture in order to help speed the reaction which will take anywhere from 8–24 hours depending on the particular operating conditions. The phase transfer catalyst may be chosen from tetraalkyl ammonium compounds, benzyl trialkyl ammonium compounds, halogenated compounds, crown ethers and mixtures thereof.

The reaction product can be isolated using conventional methods. For example, the product can be filtered in order to remove the mineral salts or acidified to about pH 2 with diluted mineral acid such as 15% chlorhydric acid or 10% sulphuric acid at a temperature of 10°–50° C. in order to eliminate excess potassium carbonate and dissolve the resulting salts in solution. The aqueous phase is then discarded. The organic phase can be allowed to crystallize over a period of 24 hours at 0° C. and then filtered in order to remove most of the triphenylphosphine oxide present in the organic phase. The liquid organic phase is then concentrated and saponified in the presence of ethanol using a strong base such as caustic soda or potassium hydroxide. Subsequently, the liquid organic phase is acidified with mineral acid to obtain a crude ambrettolic acid having predominantly cis-ethylenic unsaturation.

Another method to eliminate the triphenylphosphine oxide involves saponifying the organic phase after acidification of the reaction mixture in the presence of alcohol using a mineral base such as sodium hydroxide and then quenching with an appropriate amount of water to ensure that the salt of the resulting ambrettolic acid remains in the aqueous phase and that the triphenylphosphine oxide remains in the organic phase. After subsequent acidification of the aqueous basic solution, the crude ambrettolic acid can be separated by decanting.

The ambrettolic acid can be cyclized using conventional processes such as that disclosed in U.S. Pat. No. 4,014,902 (Tseng), the disclosure of which is hereby incorporated by reference. In particular, the glycerine polyesters of the ambrettolic acid are prepared and then depolymerized by transesterification in the presence of a mineral base such as potassium hydroxide. The resulting ambrettolide is continuously distilled off from the reaction media by azeotropic cohobation with glycerine under vacuum.

The resultant cis-isoambrettolide (Product I) is obtained with a purity of 85–90% and can be further purified by distillation, if desired. Product I was found to have the ambery or musky fragrance characteristic of the natural Product III derived from ambrette seed oil.

Synthesis of Product II (cis-oxacycioheptadec-12-en-2-one)

The preferred method of synthesizing Product II begins with the commercial product, bromo-11-undecanoic acid. The first step in the process is a conventional esterification reaction to convert the bromo-11-undecanoic acid to its corresponding $C_1$–$C_{10}$ alkyl ester and more preferably to the corresponding methyl or ethyl ester.

The bromo-11-undecanoic alkyl ester is then reacted with oxo-5-pentanol in a Wittig-type phase transfer reaction to obtain a predominance of products having cis-ethylenic unsaturation. Oxo-5-pentanol is a commercially available product which can be made by, for example, hydration of dihydropyran. The bromo-11-undecanoic alkyl ester is reacted with the oxo-5-pentanol under the same conditions as are specified above for the reaction of 6-bromohexyl acetate with the oxo-10-decanoate in the preparation of Product I.

The reaction product can be treated using conventional methods. Again, as described above, the ambrettolic acid can be isolated in the aqueous phase by saponification of the reaction product. The cyclization of the ambrettolic acid is carried out according to the method above and the desired product is distilled off from the reaction mixture by azeotropic cohobation with the glycerine under vacuum.

The isoambrettolide obtained has predominantly the cis-configuration and is about 85–90% pure. Further purification can be accomplished by rectification under vacuum in order to obtain substantially pure Product II. Product II was found to have the ambery or musky fragrance characteristic of the natural Product III derived from ambrette seed oil.

Uses of Products I–II to Impart a Fragrance

In a further embodiment, the present invention relates to a method of imparting an ambery or musky fragrance to a fragrance composition. The method includes the step of incorporating in the composition an effective amount of at least one fragrant compound selected from the Products I–II to impart an ambery or musky fragrance to said composition. Products I–II may be added to the composition in an amount of from 0.1–20% by weight, and more preferably 0.5–5% by weight, based on the total weight of the composition.

Typically, Products I–II will be added to one of two types of compositions, either a fragrance composition which is designed to be added to an end product in order to provide fragrance to that product, or directly to an end product in order to impart an ambery or musky fragrance thereto. In the former case, larger amounts of about 0.1–20% by weight of the Products I–II, and more preferably about 0.5–5% by weight of the Products I–II will be added to the fragrance composition, based on the total weight of the composition. In the latter case, significantly smaller amounts on the order of about 0.0003–2% by weight are added to end products, based on the total weight of such end products.

Fragrance Compositions Including Products I–II

In another embodiment, the present invention relates to a fragrance composition which includes one or more fragrant compounds at least one of which is one of Products I–II. Preferably Products I–II comprise 0.1–20% by weight of the total weight of such fragrance compositions and more preferably Products I–II comprise 0.5–5% by weight of the total weight of the fragrance compositions.

End Products Including Products I–II

Products I–II may also be directly included in end products or Products I–II may be incorporated into end products as a component of the fragrance composition described above. In either case, typical end products into which Products I–II may be incorporated include perfumes, toilet waters, cosmetic preparations, soaps, detergents, household products and industrial products including, but not limited to, air care products, toilet care products, surface care products, paints, masking agents for diesel fuels or gasoline, and heavy duty detergents. Either one or both of Products I-II may be incorporated in any particular product, as desired. Preferably, such end products include 0.0003–2% by weight of one or more of the Products I-II.

The following examples are provided to illustrate the invention.

EXAMPLE 1

Preparation of cis-Oxocycloheptadec-11-en-2-one (Product I)

1. Preparation of 6-bromohexyl acetate

In a one liter glass reactor equipped with magnetic stirrer, a thermometer and a 30 cm Vigreux column with a water separator, were mixed together:

72 g 1,6-hexanediol, 120 g 48% bromohydric acid, 36 g acetic acid, and 480 g toluene.

The reaction medium was then refluxed with stirring, and water was constantly removed from the reactor by azeotropic distillation. The temperature in the reaction medium went up from 90° C. to 115° C. in 5 to 6 hours, after which water removal was stopped.

The toluene solvent was concentrated under a slight vacuum and was put aside for recycle to a subsequent process.

The residue was added to 8 g of acetic anhydride and refluxed at 115° C.–120° C. for 2 hours to complete the acetylation reaction. The resulting product was then transferred into a distillation apparatus. The acetic acid was concentrated under vacuum (20 mm Hg) before fractionation under a pressure of 3 mm Hg.

The following products were obtained:

10 g dibromo-1,6-hexane to be recycled ($T_b$ 65° C.).

110 g 6-bromohexyl acetate ($T_b$ 78°–80° C.), and 12 g hexanediol-1,6-diacetate ($T_b$ 100°–102° C.).

The dibromo-1,6-hexane can be recycled by refluxing 3 hours with 3.3 g of dry sodium acetate in 6.6 g acetic acid. After separation of the sodium bromide, one obtained a nearly quantitative mixture containing 25% dibromo-1,6-hexane, 50% 6-bromohexyl acetate and 25% hexanediol-1-6-diacetate.

After vacuum distillation, the dibromo-1,6-hexane was recycled and the hexanediol-1,6-diacetate was recycled to a new operation using hexandiol-1,6 as previously described. The overall yield of 6-bromohexyl acetate with respect to the hexanediol-1,6 was 95%.

2. Wittig reaction

In a one liter glass reactor equipped with mechanical agitation, a thermometer and a condensing column with a water separator, were mixed:

96 g 6-bromohexyl acetate of 98% purity, 113 g triphenylphosphine, and 96 g toluene.

The reaction mixture was refluxed with constant agitation for 16 hours to produce the triphenyl phosphonium salt of 6-bromohexyl acetate. After cooling to about 50°–60° C., 90 g potassium carbonate, 15 g n-butanol, 2 g tetrabutylammonium bromide and 1 g water were added to the mixture. The resulting mixture was refluxed and then, 80 g of 94% pure methyl-oxo-10-decanoate was added over 2 hours at 112° C.–115° C. The temperature was maintained at 115° C.–120° C. with stirring for an additional 16 hours.

After cooling to 40° C., the reaction mixture was slowly acidified using 130 g 32% chlorhydric acid diluted in 200 g water. The aqueous phase was discarded and the organic phase was saponified by adding 96 g caustic soda and 160 g of 96% ethanol, with agitation and then refluxed for 2 hours. After cooling, 800 g water was added. The resulting mixture was agitated and then allowed to settle. The toluene phase containing triphenyl oxide was discarded.

The aqueous phase was acidified to pH 2 with 160 g of 32% chlorhydric acid diluted with 200 g water at 30° C.–40° C. in the presence of 100 g toluene. After washing with water at pH 4–5, the toluene phase was concentrated under a reduced pressure, thus obtaining 138 g crude ambrettolic acid which can be used directly for the cyclization step.

The cyclization was performed using known methods (see for instance the U.S. patents by TSENG CHING cited above). From the cyclization reaction, 60 g of cis-oxacyclopheptadec-11-en-2 one containing 87% cis-derivative and 12% trans-derivative was obtained (as determined by GLC analysis). The boiling point was 125°–128° C. at a pressure of 0.2 mm Hg.

EXAMPLE 2

Preparation of cis-Oxocycloheptadec-12-en-2-one (Product II)

In a 0.5 liter glass reactor equipped with mechanical stirring, a thermometer and a condensing column with a water separator, the following ingredients were mixed:

88.2 g ethyl bromo-11-undecanoate, 80 g triphenylphosphine, and 80 g toluene.

The resulting mixture was refluxed for 16 hours with agitation to ensure the formation of the phosphonium salt. After cooling to about 50° C., 64 g potassium carbonate, 8 g of 96% ethanol, 32 g oxo-5-pentanol and 0.3 g water were added with agitation. The mixture was then refluxed with agitation for 16 hours. After cooling to 20° C., the mineral salts were filtered off, then rinsed with 30 g toluene.

The resulting organic phases were combined, then concentrated under vacuum and the resulting product was allowed to crystallize 24 hours at 0° C. The triphenylphosphine oxide which had crystallized was filtered on sintered glass and then washed with 40 g of cold methylcyclohexane. After concentration of the solvent under vacuum, the crude ethyl ester of ambrettolic acid (approximately 110 g) was obtained.

This ester can be directly transesterified with potassium hydroxide for instance, in the presence of glycerine which allows the one-step azeotropic cohobation of the resulting ambrettolide, under vacuum, as previously described.

Alternatively, the ester may be saponified to obtain the ambrettolic acid. The crude ambrettolic acid obtained by saponification was transformed into its glycerine polyester by heating under a slight vacuum at 180° C. for a period of 4 to 5 hours. The resulting polyesters were then depolymerized in the presence of a mineral base, potassium hydroxide, to give ambrettolide which was distilled off by azeotropic distillation using glycerine. After fractionation, 43 g of cis-oxacyclopheptadec-12-en-2-one (Product II) containing 86% of the cis-derivative and 13% of the trans-derivative, was obtained (as determined by GLC analysis) ($T_b$ 125° C.–128° C. at 0.2 mm Hg).

EXAMPLE 3

Fragrance Compositions

| Formula for alcoholic fragrance application | |
|---|---|
| Products | Dosages (g) |
| Bergamot oil | 50 |
| Lemon oil | 150 |
| Bitter orange oil | 50 |
| Orange oil | 150 |
| Mandarin oil | 50 |
| Litsea Cubeba oil | 50 |
| Rosemary oil | 30 |
| Petitgrain oil | 50 |
| Treemoss absolute | 20 |
| Hexylcinnamic aldehyde | 100 |
| Linalool | 50 |
| Hydroxycitronellal | 50 |
| Δ-10-cis Isoambrettolide - Product (I) | 100 |
| | 900 |

Olfactive description: cologne, citrusy, flowery, musky. The musky note of isoambrettolide fix the fresh notes.

EXAMPLE 4

| Formula for soap fragrance application | |
|---|---|
| Products | Dosages (g) |
| Bergamot oil | 50 |
| Lemon oil | 50 |
| Armoise oil | 20 |
| Lavender oil | 50 |
| Clove buds oil | 30 |
| Geranium oil | 100 |
| Patchouli oil | 100 |
| Sandalwood oil | 100 |
| Treemoss absolute | 20 |
| Labdanum absolute | 20 |
| Tonka beans absolute | 10 |
| Hexylcinnamic aldehyde | 150 |
| Linalool | 50 |
| Hydroxycitronellal | 50 |
| Methylionones | 100 |
| Δ-11-cis Isoambrettolide - Product (II) | 100 |
| | 1000 |

Olfactive description: fougere, woody, musky. The musky note of isoambrettolide reinforces the ambery woody undertones of the mixture.

The foregoing examples were presented for the purpose of illustration and description only and are not to be construed as limiting the invention in any way. The scope of the invention is to be determined from the claims appended hereto.

We claim:

1. A process for the preparation of an ω-haloalkyl carboxylic ester comprising the step of reacting an α-ω-alkanediol with an halohydric acid in the presence of an aliphatic carboxylic acid in an inert organic solvent which is capable of forming an azeotrope with water.

2. A process as claimed in claim 1 wherein the organic solvent is selected from the group consisting of toluene, cyclohexane, methyl-cyclohexane, xylene and mixtures thereof.

3. A process as claimed in claim 2 wherein the ester comprises an ω-bromoalkyl ester and the halohydric acid comprises bromohydric acid.

4. A process as claimed in claim 3 wherein the aliphatic carboxylic acid comprises acetic acid and the α-ω-alkanediol comprises 1,6-hexanediol.

5. A process for the preparation of at least one product of the formulae I–II

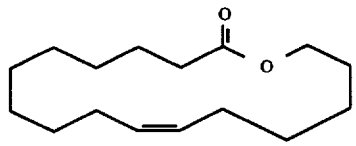

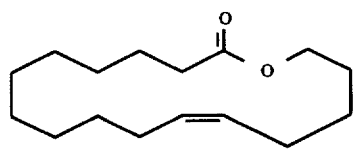

which process comprises the step of condensing a phosphonium salt of an ω-haloalkyl carboxylic ester with a compound selected from the group consisting of aldehyde-alcohols and aldehyde-esters, using a solid-liquid phase transfer reaction.

6. A process as claimed in claim 5 wherein the condensation step is carried out in the presence of water and at least one salt selected from the group consisting of alkali metal carbonates and alkaline earth metal carbonates.

7. A process as claimed in claim 6 wherein the condensation step is carried out in the further presence of a phase transfer catalyst.

8. A process as claimed in claim 7 wherein the phase transfer catalyst is selected from the group consisting of tetraalkyl ammonium, benzyl trialkyl ammonium, halogenated compounds, crown ethers and mixtures thereof.

9. A process as claimed in claim 8 wherein the condensation step is carried out in a solvent selected from the group consisting of toluene, cyclohexane, methyl-cyclohexane, dioxane, dichloro-1,2-ethane and mixtures thereof.

10. A process as claimed in claim 9 wherein the solvent further comprises at least one other solvent selected from the group consisting of lower aliphatic alcohols.

11. A process as claimed in claim 5 further comprising the step of preparing a phosphonium salt of an ω-haloalkyl ester prior to the condensation step by reacting an ω-haloalkyl ester with triphenylphosphine in an inert organic solvent.

12. A process as claimed in claim 11 further comprising the step of preparing an ω-haloalkyl ester prior to the step of preparing said phosphonium salt by reacting an α-ω-alkanediol with an halohydric acid in the presence of an aliphatic carboxylic acid and in an inert organic solvent which is capable of forming an azeotrope with water.

13. A process as claimed in claim 12 wherein the organic solvent for the reaction of an α-ω-alkanediol with an halohydric acid is selected from the group consisting of toluene, cyclohexane, methyl-cyclohexane, xylene, aliphatic alcohols and mixtures thereof.

14. A process as claimed in claim 13 wherein the ester comprises an ω-bromoalkyl ester and the halohydric acid comprises bromohydric acid.

15. A process as claimed in claim 14 wherein the aliphatic carboxylic acid comprises acetic acid and the alkanediol comprises 1,6-hexanediol.

\* \* \* \* \*